US009373165B2

(12) United States Patent
Azordegan et al.

(10) Patent No.: US 9,373,165 B2
(45) Date of Patent: Jun. 21, 2016

(54) ENHANCED PATTERNED WAFER GEOMETRY MEASUREMENTS BASED DESIGN IMPROVEMENTS FOR OPTIMAL INTEGRATED CHIP FABRICATION PERFORMANCE (71) Applicant: KLA-Tencor Corporation, Milpitas, CA (US)

(72) Inventors: Amir Azordegan, Santa Clara, CA (US); Pradeep Vukkadala, Fremont, CA (US); Craig MacNaughton, Los Gatos, CA (US); Jaydeep Sinha, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/520,998

(22) Filed: Oct. 22, 2014

(65) Prior Publication Data
US 2016/0071260 A1    Mar. 10, 2016

Related U.S. Application Data (60) Provisional application No. 62/048,114, filed on Sep. 9, 2014.

(51) Int. Cl.
*G06F 17/50* (2006.01)
*G06T 7/00* (2006.01)
*G01B 11/24* (2006.01)
*G01N 21/95* (2006.01)

(52) U.S. Cl.
CPC .............. *G06T 7/0006* (2013.01); *G01B 11/24* (2013.01); *G01N 21/9501* (2013.01); *G06F 17/5081* (2013.01); *G06T 2207/30148* (2013.01)

(58) Field of Classification Search
CPC ... G06F 17/5081; G06T 7/0006; G01B 11/24; G01N 21/9501
USPC .................................................... 716/52, 123
See application file for complete search history.

(56) References Cited

U.S. PATENT DOCUMENTS

| | | | |
|---|---|---|---|
| 7,207,017 B1 * | 4/2007 | Tabery ............... | G06F 17/5081 716/52 |
| 7,598,492 B1 | 10/2009 | Krzeczowski et al. | |
| 2002/0171873 A1 * | 11/2002 | Chang ............... | H04N 1/40075 358/3.06 |
| 2005/0076316 A1 * | 4/2005 | Pierrat ............... | G06F 17/5036 716/52 |
| 2008/0203589 A1 | 8/2008 | Bailey et al. | |
| 2010/0309308 A1 | 12/2010 | Saphier et al. | |
| 2012/0019650 A1 | 1/2012 | Perriollat | |
| 2013/0121617 A1 | 5/2013 | Serrels et al. | |

OTHER PUBLICATIONS

C.A. Glasbey et al., Alignment and sub-pixel interpolation of images using Fourier methods, Journal of Applied Statistics, Jul. 20, 2007, pp. 217-230, vol. 34, Issue 2, Printed online at: http://www.bioss.ac.uk/people/chris/landsat.pdf.
Sina Farsiu et al., Fast and Robust Multiframe Super Resolution, IEEE Transactions on Image Processing, Oct. 2004, vol. 13, No. 10, pp. 1327-1344, © 2004 IEEE.
PCT Search Report for PCT/US2015/049158 dated Dec. 10, 2015, 11 pages.

* cited by examiner

*Primary Examiner* — Vuthe Siek
(74) *Attorney, Agent, or Firm* — Suiter Swantz pc llo (57) ABSTRACT Methods and systems enabling ultra-high resolution topography measurements of patterned wafers are disclosed. Measurements obtained utilizing the ultra-high resolution metrology may be utilized to improve wafer metrology measurement accuracies. Additionally, measurements obtained utilizing the ultra-high resolution metrology may also be utilized to provide feedback and/or calibration control to improve fabrication and design of wafers.

26 Claims, 8 Drawing Sheets

ENHANCED PATTERNED WAFER GEOMETRY MEASUREMENTS BASED DESIGN IMPROVEMENTS FOR OPTIMAL INTEGRATED CHIP FABRICATION PERFORMANCE

CROSS-REFERENCE TO RELATED APPLICATIONS

The present application claims the benefit under 35 U.S.C. §119(e) of U.S. Provisional Application Ser. No. 62/048,114, filed Sep. 9, 2014. Said U.S. Provisional Application Ser. No. 62/048,114 is hereby incorporated by reference in its entirety.

TECHNICAL FIELD

The disclosure generally relates to the field of wafer surface metrology, and particularly to systems and methods for enhancement of wafer geometry measurements and wafer design improvements based on the enhanced wafer geometry measurements.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Wafers are available in a variety of sizes. They may also be patterned or presented as bare wafers. Interferometer wafer metrology systems, such as WaferSight metrology system from KLA-Tencor, may scan both the front and back surfaces of a wafer at the same time. By combining wafer shape, edge roll-off, thickness or flatness, and topography measurements in a single scan, such wafer metrology tools may provide complete data sets that are necessary for topography and wafer geometry monitoring in wafer manufacturing.

It is noted, however, that the resolutions of the imaging devices utilized in some of the interferometer wafer metrology systems may not be able to fully resolve certain patterned wafer surfaces, limiting the accuracies of such metrology systems in patterned wafer geometry. Therein lies a need for systems and methods for enhancing wafer geometry measurements, particularly for patterned wafers, and utilizing the enhanced measurements for various monitoring and design purposes.

SUMMARY

The present disclosure is directed to a resolution enhancement method for wafer geometry measurements. The method includes: acquiring a plurality of wafer geometry images for at least one substantially identical portion of at least one wafer, wherein each of the plurality of wafer geometry images is acquired with a different sub-pixel modulation in spatial phase; and jointly processing the plurality of wafer geometry images utilizing at least one statistical treatment to produce a resolution-enhanced representation of the plurality of wafer geometry images.

A further embodiment of the present disclosure is directed to a wafer geometry based pattern layout analysis method. The method includes: obtaining a resolution-enhanced topography map for at least one portion of at least one wafer etched according to a pattern layout; identifying at least one region within the resolution-enhanced topography map as having high frequency topography variations; and modifying the pattern layout to include at least one dummy-fill within the at least one identified region.

In addition, a further embodiment of the present disclosure is directed to a wafer geometry measurement system. The system includes an imaging device. The imaging device is configured to acquire a plurality of wafer geometry images for at least one substantially identical portion of at least one wafer, wherein each of the plurality of wafer geometry images is acquired with a different sub-pixel modulation in spatial phase. The system also includes a processor in communication with the imaging device. The processor is configured to jointly process the plurality of wafer geometry images utilizing at least one statistical treatment to produce a resolution-enhanced representation of the plurality of wafer geometry images.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Wafer metrology systems, such as WaferSight metrology system from KLA-Tencor, may use double-Fizeau interferometry to make high resolution (e.g., 125 um-500 um pixel width) surface height measurements of front and/or back surface of patterned wafers. Such wafer metrology systems capable of measuring patterned wafers may be referred to as patterned wafer geometry (PWG) measurement systems. It is noted that the resolution provided by a PWG measurement system may be limited by the resolution of the imaging device(s) utilized, and various practical reasons may curtail resolution improvement via hardware changes. Mathematical algorithms are typically utilized to treat the obtained measurement maps to further extract wafer shape maps, front/back topography maps (such as nanotopography), flatness, thickness variation maps and the like.

It is contemplated that the obtained measurement maps for a single wafer or multiple wafers at a single process step or across multiple process steps may be further processed to estimate/calculate local stresses induced in the wafer (e.g., within-die variations of spatial wavelengths of a few 100 s of microns), local distortions induced by wafer processes that may lead to overlay and yield issues for downstream processes, polishing problems induced by local topography variations, as well as other measurements of interest. It is also contemplated that the various types of estimated values may be obtained before and/or after a given process step, enabling rapid feedback with regards to potential process issues caused by that particular process step. In addition, potential process issues may also be localized to particular regions across the wafer or within a die, and these potential process issues may be visualized and/or utilized in various different manners to enhance the wafer manufacturing process.

It is noted that the accuracies and the effectiveness of the various types of measurements described above can be improved if the resolution of the PWG surface height measurements can be enhanced beyond the resolution limitations of the imaging devices. Embodiments in accordance with the present disclosure may therefore enable ultra-high resolution topography (e.g., surface height) measurements of patterned wafers, and utilize measurements obtained from the ultra-high resolution metrology to further improve wafer metrology measurement accuracies.

Figure 1:
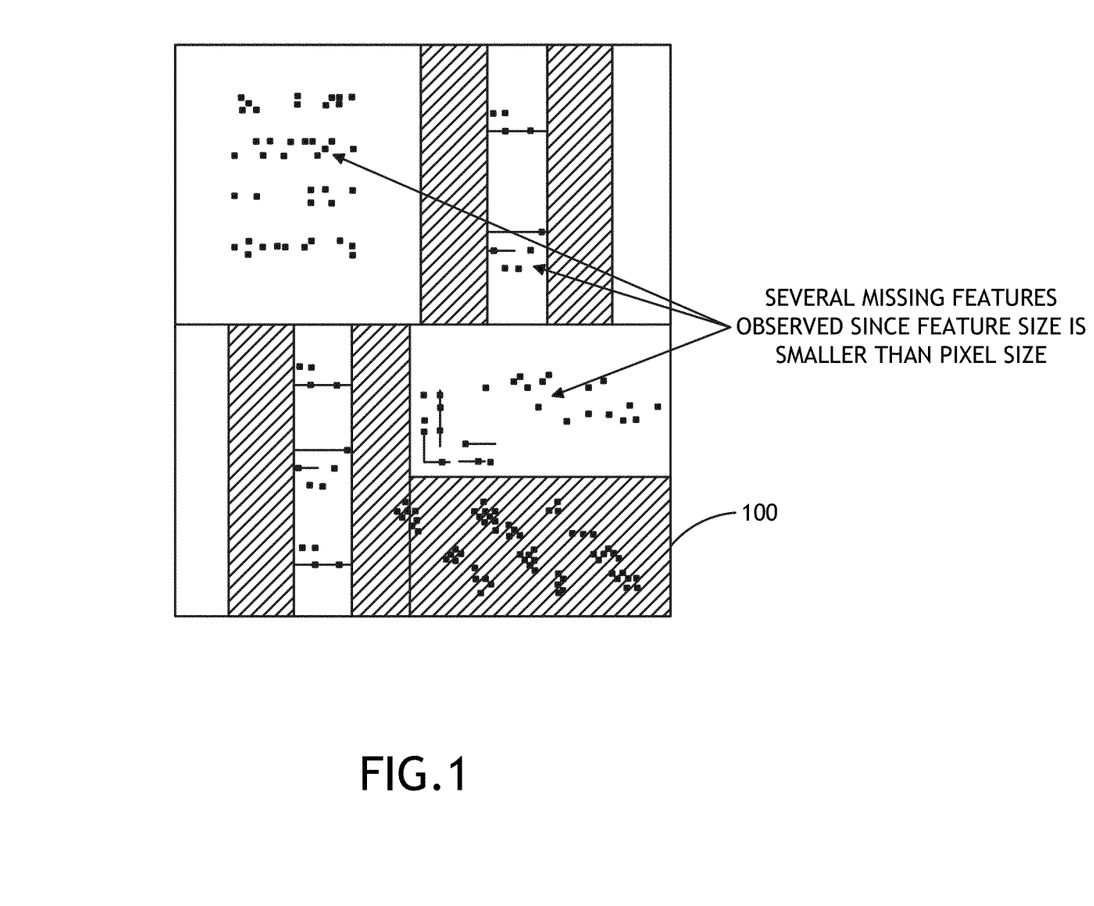
FIG. 1 is an illustration depicting a topography map.
Figure 2:
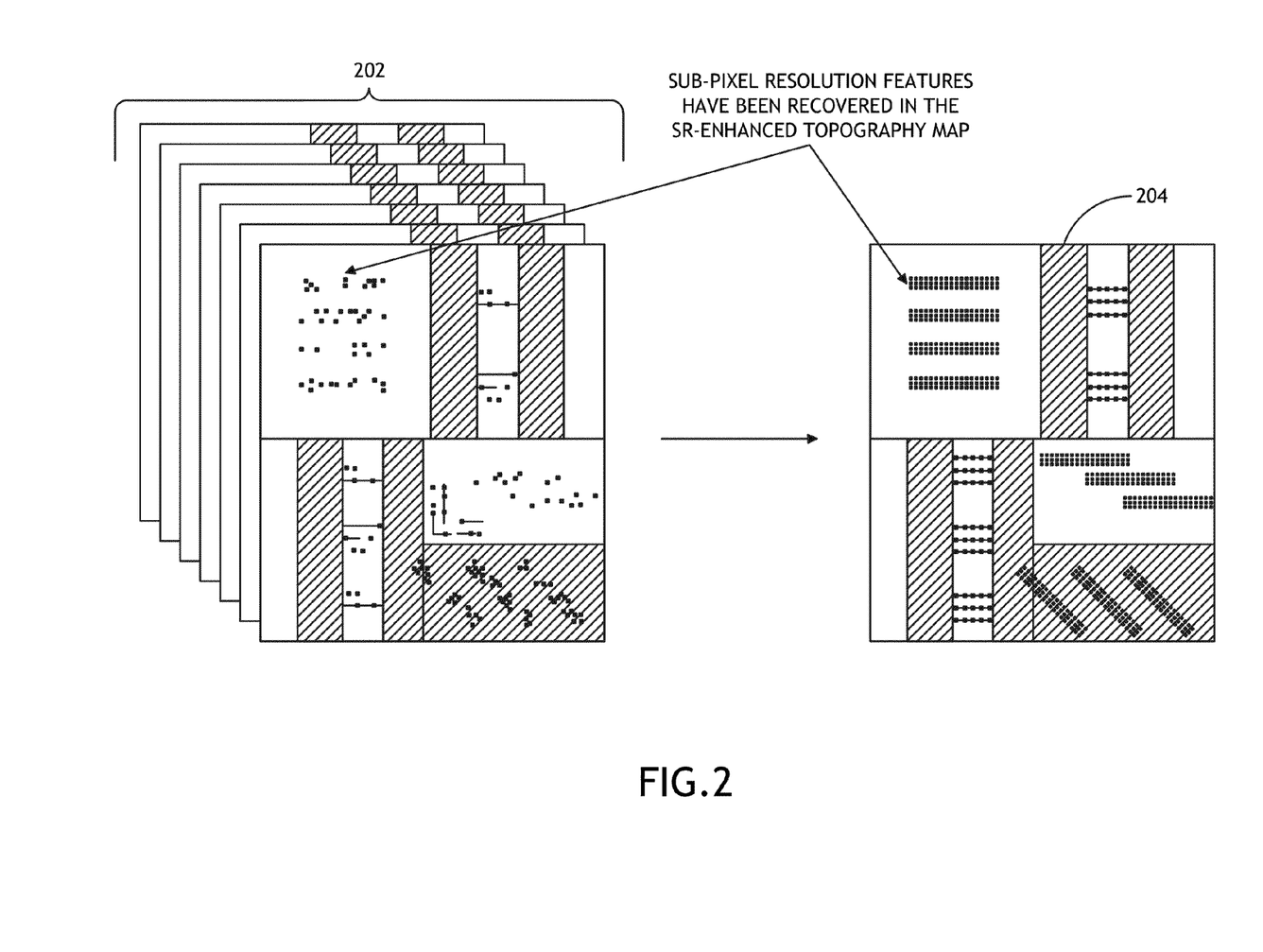
FIG. 2 is an illustration depicting generation of a resolution-enhanced topography map.

Referring generally to FIGS. 1 and 2, exemplary illustrations depicting topography maps (wafer surface height differences) are shown. It is to be understood that a PWG measurement system utilized to obtain such topography maps may be configured to obtain topography map(s) of a full wafer surface or a given portion of the full wafer surface; however, for illustrative purposes, the topography map of only a single die 100 is depicted in FIG. 1. As shown in FIG. 1, due to physical/optical limitations of the imaging device(s) utilized by the PWG measurement system, wafer surface features that are smaller than the pixel size of the imaging device(s) may be missing from the topography map 100.

It is contemplated that certain embodiments of the present disclosure may enhance the resolution to obtain topography of sub-pixel resolution features utilizing techniques such as superresolution (SR) and/or sub-pixel interpolation. Superresolution techniques adopt statistical treatment of an image acquired multiple times to infer image details beyond the standard resolution limit of the imaging device while staying within the diffraction limit. An exemplary superresolution technique is described in: Fast and Robust Multi-frame Super-resolution, S. Farsiu et al., IEEE Transactions on Image Processing, vol. 13, no. 10, pp. 1327-1344 (October 2004), which is herein incorporated by reference in its entirety. Additionally, Fourier methods such as the one reported in: Alignment and sub-pixel interpolation of images using Fourier methods, C. A. Glasbey et al., Journal of Applied Statistics, vol. 34, no. 2 (2007): 217-230, which is herein incorporated by reference in its entirety, may be used to perform sub-pixel interpolation to achieve alignment between interferometric acquisitions having sub-pixel spatial shifts. An example of superresolution and sub-pixel interpolation enhanced field-level topography map obtained from a PWG measurement system configured in accordance with embodiments of the present disclosure is shown in FIG. 2.

Figure 3:
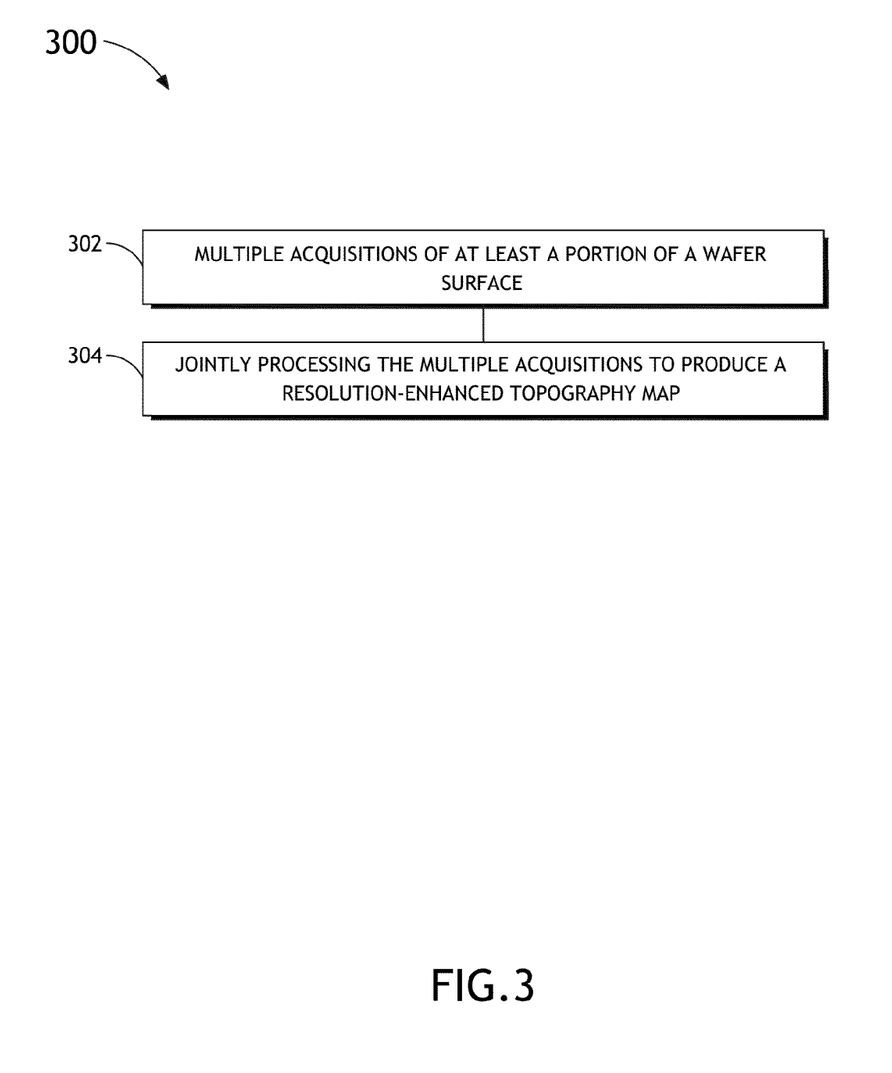
FIG. 3 is a flow diagram depicting a method for generating a resolution-enhanced topography map.

More specifically, referring generally to FIGS. 2 and 3, multiple acquisitions 202 carried out in a step 302 are jointly processed in a step 304 to obtain the resolution-enhanced topography map 204. By obtaining sufficient number of topography measurements 202 of the wafer (either obtained for the full-wafer or at the field/die-level) having sub-pixel modulation in spatial phase, the step 304 is able to calculate a topography map 204 at sub-pixel resolution much greater than the standard single-shot resolution capability of the imaging device.

It is contemplated that the aforementioned multiple acquisitions step 302 may be carried out in various different manners. For instance, in one embodiment, the relative position between the imaging device (e.g., a camera or an optical sensor) and the test specimen (e.g., a wafer) may be intentionally shifted slightly in a certain manner when the multiple acquisitions are taken. It is contemplated that this intentional shifting may be carried out physically (e.g., utilizing a mechanical actuator) and/or optically (e.g., utilizing phase shifting or modulation). Alternatively and/or additionally, shifting may occur naturally from die-to-die because the die-size (e.g., width and height) may be a non-integral multiple of pixel-size. Similarly, shifting may also occur due to natural shifts in the imagining device from acquisition to acquisition determined by location precision. It is to be understood that various other methods may also be utilized to implement the slight shifting required for the acquisition step 302. It is also to be understood that the acquisition step 302 may acquire the multiple images 202 utilizing different intensity/wavelength settings each having different levels of features detail.

It is contemplated that the acquisition step 302 may repeatedly acquire data of the same wafer (or a particular field/die of the wafer) multiple times for the multiple acquisitions. Alternatively, if repeating patterns are present on a given wafer, step 302 may obtain the full-wafer topography measurement and then divide the wafer into fields/dies corresponding to lithography-exposure field size thereby obtaining multiple measurements of essentially the same image (by nature of repeating patterns printed on the wafer). Additional processes to filter out across-wafer topography to only retain within-field topography variations may also be carried out.

It is also contemplated that once the multiple measurements are acquired, various types of resolution enhancement techniques, such as superresolution and sub-pixel interpolation techniques, may then be applied to obtain the resolution-enhanced topography map 204 as indicated in the step 304.

It is further contemplated that the resolution-enhanced topography maps as described above not only can be utilized to improve accuracies of wafer metrology measurements, but also can be utilized to improve fabrication and design of wafers. For instance, in some embodiments, resolution-enhanced topography maps may be utilized as a feedback control to improve wafer pattern layout designs.

Figure 4:
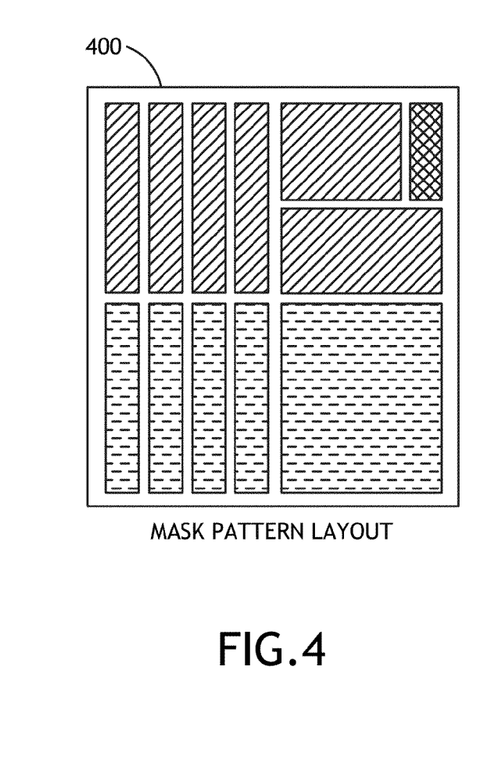
FIG. 4 is an illustration depicting a mask pattern layout schematic.
Figure 5:
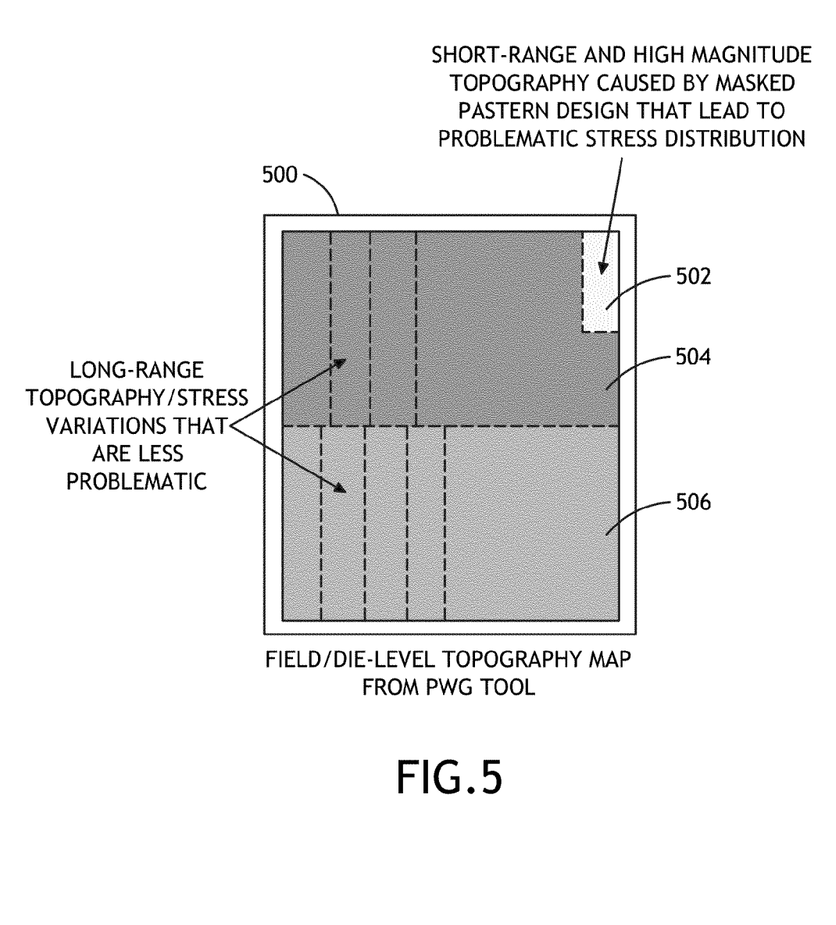
FIG. 5 is an illustration depicting a resolution-enhanced topography map obtained from a wafer having the mask pattern layout etched into it.

Referring now generally to FIGS. 4 and 5. FIG. 4 is an illustration depicting a mask pattern layout schematic 400 and FIG. 5 is an illustration depicting a resolution-enhanced topography map 500 obtained from a wafer having the mask pattern layout 400 etched into it. The term "mask pattern layout" (or simply pattern layout) refers to the arrangement of different component blocks of a mask design. It has been observed that high frequency (short spatial range) topography variations are induced within the die as a result of the mask pattern layout. Such high frequency topography can lead to local stresses and distortions that can significantly affect yield and performance.

Based on this observation, the resolution-enhanced topography map 500 may be analyzed to identify any region that may have potentially problematic stress distributions. For illustrative purposes, suppose region 502 in the resolution-enhanced topography map 500 shows signs of high frequency topography variations (e.g., above a certain threshold), while topography variations within regions 504 and 506 may occur relatively lower in frequency. This analysis may indicate that region 502 is a potential region that may experience stress distribution problems. It is contemplated that this analysis result may be utilized as a feedback to modify and improve the design of the pattern layout 400.

In some embodiments of the present disclosure, local stress distribution within the region 502 may be adjusted using a dummy-fill 602 (FIG. 6) in an effort to minimize sharp topography/stress transitions in that region. While dummy-fills are commonly used in wafers for various purposes, the techniques utilized to determine the optimal location for positioning such a dummy-fill as described above is advantageous. Positioning the dummy-fill 602 within the region 502 effectively reduces high frequency topography variations previously observed in the resolution-enhanced topography map 500, thereby reducing local stress and distortions occurring in this region.

Figure 6:
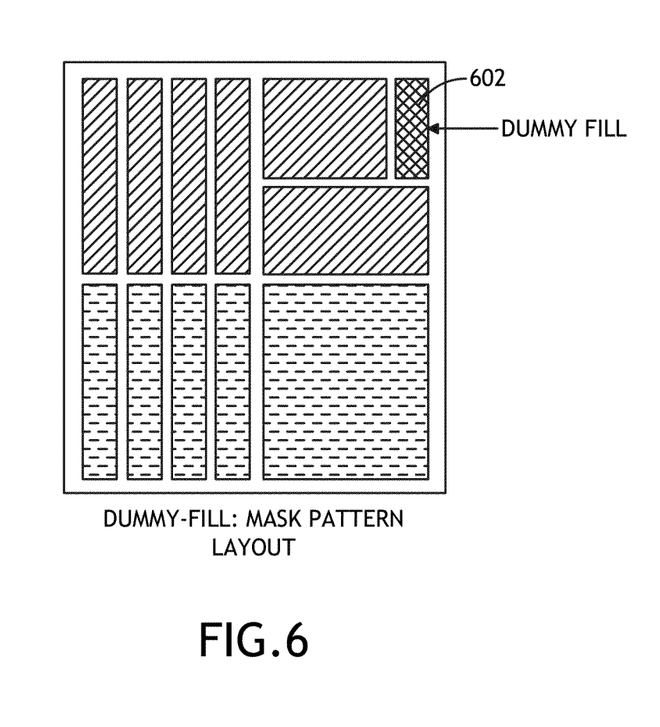
FIG. 6 is an illustration depicting a determined position for inserting a dummy-fill.
Figure 7:
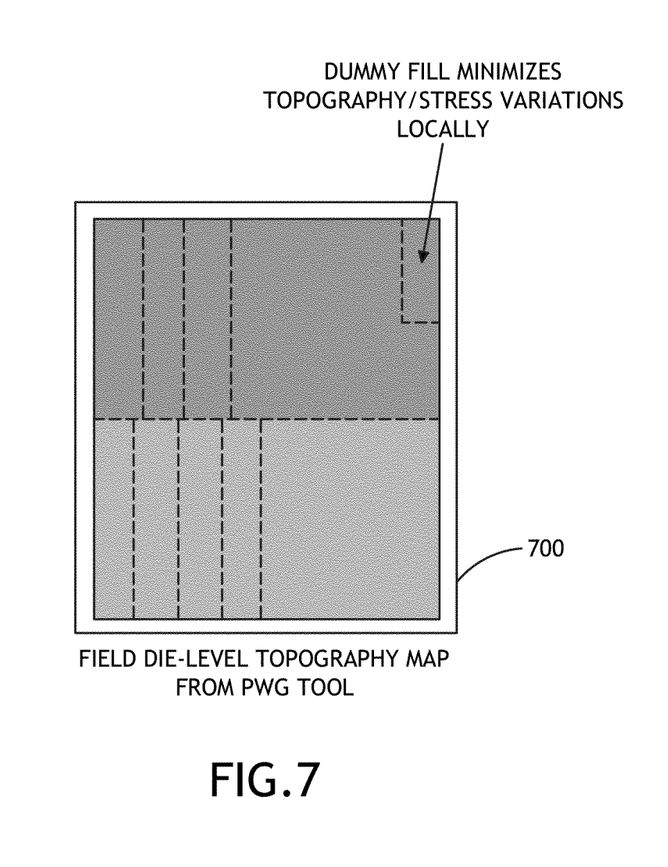
FIG. 7 is an illustration depicting a resolution-enhanced topography map obtained from a wafer having a modified mask pattern layout with dummy-fill etched into it.

It is contemplated that the effectiveness of placing the dummy-fill 602 at the determined location may be further analyzed by acquiring another resolution-enhanced topography map 700 (FIG. 7). It is to be understood that if the resolution-enhanced topography map 700 continues to show region(s) of high frequency topography variations, additional dummy-fills may be introduced to the pattern layout in a similar process as described above. It is contemplated that this process may repeat until a termination condition is reached (e.g., the region of high frequency topography variations is below a certain threshold or the like), at which point the dummy-fill optimization process may terminate.

Figure 8:
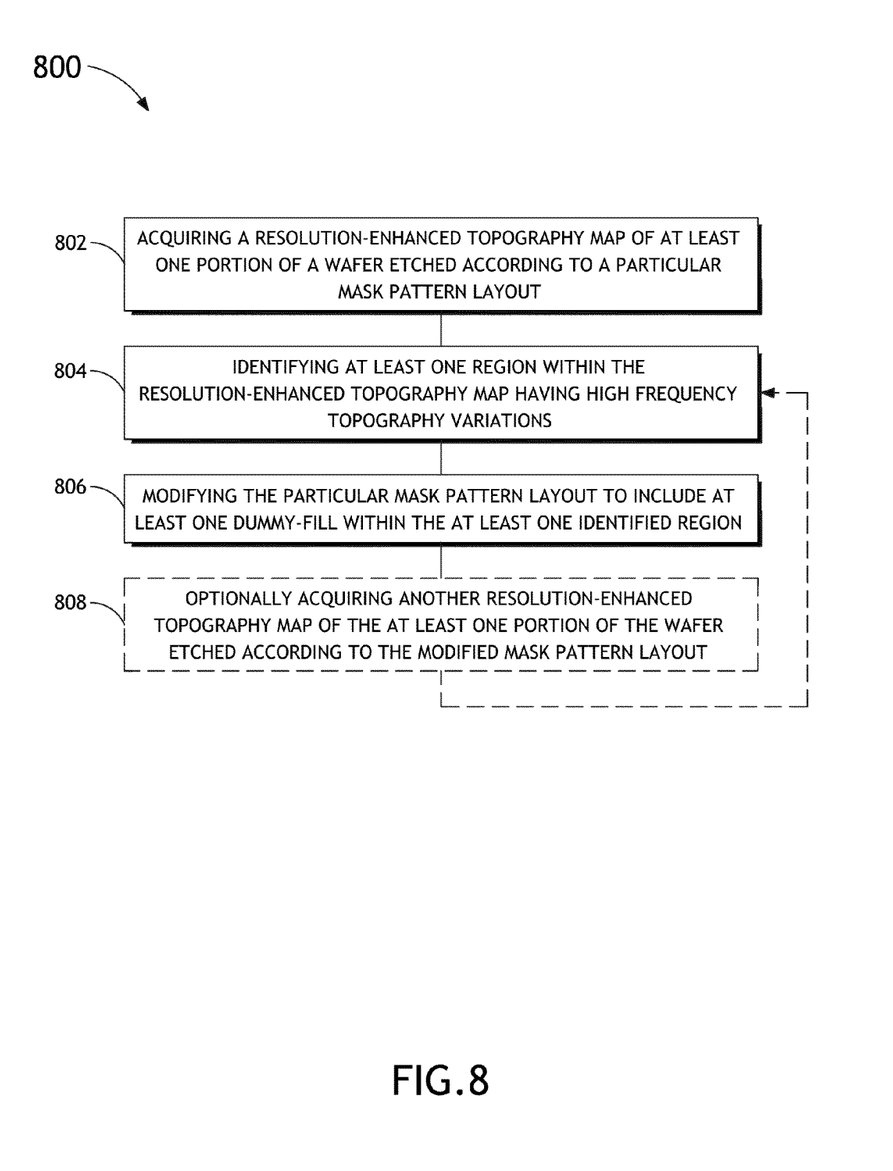
FIG. 8 is a flow diagram depicting a dummy-fill optimization method.

Referring to FIG. 8, a flow diagram depicting the dummy-fill optimization process 800 is shown. As previously described, in a step 802, a resolution-enhanced topography map of at least a portion of a wafer is acquired in a step 802. It is noted that the wafer may be etched according to a particular mask pattern layout. Subsequently, in a step 804, at least one region within the resolution-enhanced topography map may be identified as having high frequency topography variations. Since the identified region(s) may potentially have problematic stress distributions, the original mask pattern layout corresponding to such identified regions may need to be modified to include one or more dummy-fills in a step 806. In an optional step 808, another resolution-enhanced topography map may be acquired to evaluate the effectiveness of the insertion of the dummy-fill(s). As previously described, this dummy-fill optimization process 800 may repeat until a termination condition is reached.

It is contemplated that the resolution-enhanced topography maps may also be utilized to identify highly local and small fill areas throughout the die (or the entire wafer) to further improve wafer pattern layout designs in addition (or alternative) to the dummy-fill optimization techniques described above. In other words, the highly local and small fill areas identified based on the resolution-enhanced topography maps may go beyond mask pattern layout optimization and may be used to feedback design changes to the Electronic Design Automation (EDA) process where low-level circuit patterns are designed.

Figure 9:
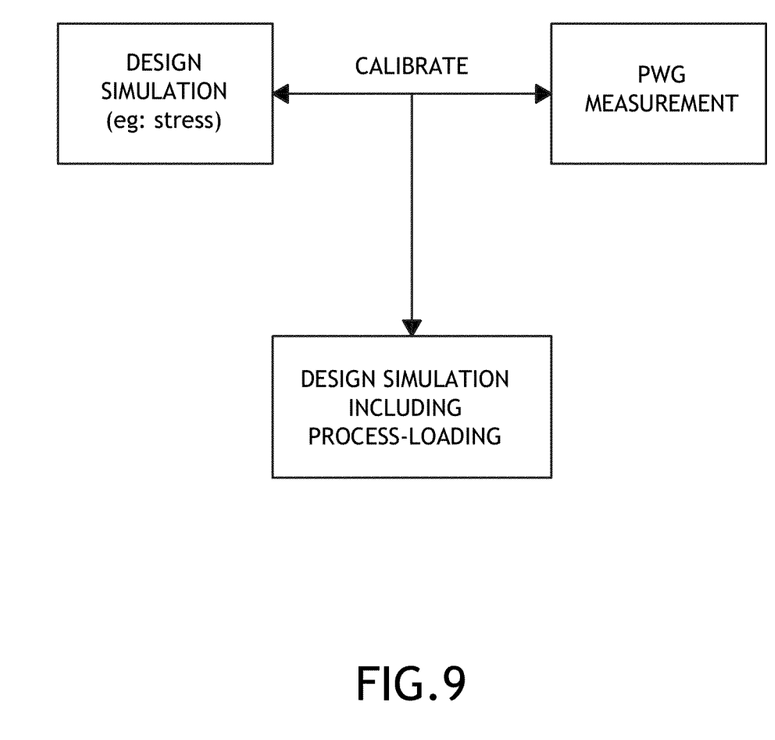
FIG. 9 is a block diagram depicting utilization of the resolution-enhanced topography map for design calibration.

It is also contemplated that the resolution-enhanced topography maps may be utilized to calibrate design simulation models. More specifically, it is noted that while simulations are performed to some extent in order to determine the effect of a design (circuit design, pattern layout, materials) on circuit performance, the simulation results are not always reliable. One critical reason for this is because simulations do not consider the effect of process-loading on the final results. For example, a design simulation may be performed to estimate stress induced by etching of a particular pattern layout design. However, the design simulation model may not be aware of state of the wafer prior to the etching process and the processes that wafer will be subjected to after the etching step, thereby affecting the quality of the simulation results. Having the resolution-enhanced topography maps may enable a more complete estimation of the impact of a given process including process-loading. The resolution-enhanced topography maps may be combined with simulation results in order to drive the design process. In addition, the resolution-enhanced topography maps may also be used to calibrate design simulation models. This is further illustrated in FIG. 9.

It is to be understood that the resolution-enhanced topography maps may be utilized to improve performance of various other processes related to wafer fabrication. For instance, the resolution-enhanced topography maps may be utilized in conjunction with existing techniques to facilitate defect detection processes. In another example, the resolution-enhanced topography maps may be used as feed-forward and/or feedback controls for a polishing process such as Chemical Mechanical Polishing (CMP). It is contemplated that various other types of wafer processes may take into account the resolution-enhanced topography maps as described above without departing from the spirit and scope of the present disclosure.

Figure 10:
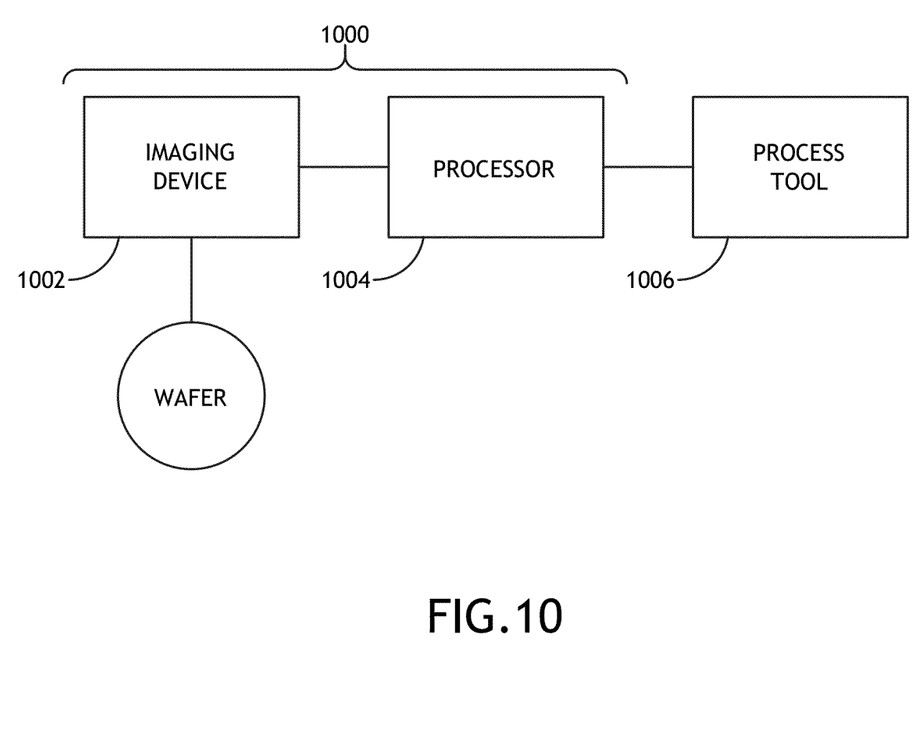
FIG. 10 a block diagram depicting a measurement system capable of providing ultra-high resolution topography measurements of patterned wafers.

FIG. 10 is a block diagram depicting a measurement system 1000 capable of providing ultra-high resolution topography measurements of patterned wafers. As previously described, resolutions of the measurements taken utilizing the imaging device(s) 1002 may be further enhanced by the processor 1004. The processor 1004 may utilize resolution enhancement techniques such as superresolution (SR) and/or sub-pixel interpolation to obtain topographies that may contain of sub-pixel resolution features. It is contemplated that the processor 1004 may be implemented as a standalone processing device or as an embedded/integrated component of the measurement system 1000. It is also contemplated that the processor 1004 may provide its output to various process tools 1006, including, but not limited to, lithography focus control, CMP, as well as other semiconductor process and/or design tools as described above.

It is contemplated that while some of the examples above referred to certain specific process tools, the systems and methods in accordance with the present disclosure are applicable to other types of process tools, which may also benefit from resolution-enhanced measurements without departing from the spirit and scope of the present disclosure. In addition, it is contemplated that the specific superresolution and sub-pixel interpolation techniques previously mentioned are merely exemplary; different superresolution and sub-pixel interpolation techniques may be utilized without departing from the spirit and scope of the present disclosure. Furthermore, the term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented in various wafer geometry measurement tools as sets of instructions executed by one or more processors, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A resolution enhancement method for wafer geometry measurements, the method comprising:
   acquiring a plurality of wafer geometry images for at least one substantially identical portion of at least one wafer, wherein each of the plurality of wafer geometry images is acquired with a different sub-pixel modulation in spatial phase; and
   jointly processing the plurality of wafer geometry images utilizing at least one statistical treatment to produce a resolution-enhanced representation of the plurality of wafer geometry images.

2. The method of claim 1, wherein the at least one statistical treatment includes at least one of: a superresolution technique and a sub-pixel interpolation technique.

3. The method of claim 1, wherein intentional shifting of an image sensor relative to the at least one wafer is utilized to provide the sub-pixel modulation in spatial phase.

4. The method of claim 1, wherein varying at least one of: an intensity and a wavelength of an interferometer is utilized to provide the sub-pixel modulation in spatial phase.

5. The method of claim 1, wherein the plurality of wafer geometry images are acquired by repeatedly acquiring wafer geometry images for at least one substantially identical portion of a plurality of wafers.

6. The method of claim 1, wherein the plurality of wafer geometry images are acquired by acquiring a wafer geometry image of a wafer and obtaining the plurality of wafer geometry images representing repeating patterns present within the wafer.

7. The method of claim 1, wherein the resolution-enhanced representation represents a resolution-enhanced topography map of the at least one portion of the at least one wafer.

8. The method of claim 7, further comprising:
   identifying at least one region within the resolution-enhanced topography map having high frequency topography variations;
   determining a location for positioning at least one dummy-fill within the at least one identified region based on the at least one identified region; and
   producing a modified pattern layout corresponding to the at least one wafer to include the at least one dummy-fill within the at least one identified region.

9. The method of claim 7, further comprising:
   calibrating a design simulation model at least partially based on the resolution-enhanced topography map.

10. A wafer geometry based pattern layout analysis method, the method comprising:
    obtaining a first resolution-enhanced topography map for at least one portion of at least one wafer etched according to a pattern layout;
    identifying at least one region within the first resolution-enhanced topography map as having high frequency topography variations;
    modifying the pattern layout to include at least one dummy-fill within the at least one identified region;
    obtaining a second resolution-enhanced topography map for the at least one portion of the at least one wafer etched according to the modified pattern layout;
    determining an effectiveness of the modified pattern layout; and
    etching a subsequent wafer based on the modified pattern layout when the modified pattern layout is determined to be effective.

11. The method of claim 10, wherein said determining an effectiveness of the modified pattern layout further comprises:
    determining whether an additional pattern layout modification is needed based on whether the second resolution-enhanced topography map has any region with high frequency topography variations.

12. The method of claim 10, wherein obtaining a first resolution-enhanced topography map for at least one portion of at least one wafer further comprises:
    acquiring a plurality of wafer geometry images for the portion of the at least one wafer, wherein each of the plurality of wafer geometry images is acquired with a different sub-pixel modulation in spatial phase; and
    jointly processing the plurality of wafer geometry images utilizing at least one statistical treatment to produce the first resolution-enhanced topography map.

13. The method of claim 12, wherein the at least one statistical treatment includes at least one of: a superresolution technique and a sub-pixel interpolation technique.

14. The method of claim 12, wherein intentional shifting of an image sensor relative to the at least one wafer is utilized to provide the sub-pixel modulation in spatial phase.

15. The method of claim 12, wherein varying at least one of: an intensity and a wavelength of an interferometer is utilized to provide the sub-pixel modulation in spatial phase.

16. The method of claim 12, wherein the plurality of wafer geometry images are acquired by repeatedly acquiring wafer geometry images for at least one portion of a plurality of wafers.

17. The method of claim 12, wherein the plurality of wafer geometry images are acquired by acquiring a wafer geometry image of a wafer and obtaining the plurality of wafer geometry images representing repeating patterns present within the wafer.

18. A wafer geometry measurement system, the system comprising:
    an imaging device configured to acquire a plurality of wafer geometry images for at least one substantially identical portion of at least one wafer, wherein each of the plurality of wafer geometry images is acquired with a different sub-pixel modulation in spatial phase; and
    a processor in communication with the imaging device, the processor configured to jointly process the plurality of wafer geometry images utilizing at least one statistical treatment to produce a resolution-enhanced representation of the plurality of wafer geometry images.

19. The system of claim 18, wherein the at least one statistical treatment includes at least one of: a superresolution technique and a sub-pixel interpolation technique.

20. The system of claim 18, wherein relative positions of the imaging device and the at least one wafer are shifted to provide the sub-pixel modulation in spatial phase.

21. The system of claim 18, wherein at least one of: an intensity and a wavelength of an interferometer of the wafer geometry measurement system is varied to provide the sub-pixel modulation in spatial phase.

22. The system of claim 18, wherein the imaging device acquires the plurality of wafer geometry images by repeatedly acquiring wafer geometry images for at least one substantially identical portion of a plurality of wafers.

23. The system of claim 18, wherein the imaging device acquires the plurality of wafer geometry images by acquiring a wafer geometry image of a wafer and obtaining the plurality of wafer geometry images representing repeating patterns present within the wafer.

24. The system of claim 18, wherein the resolution-enhanced representation represents a resolution-enhanced topography map of the at least one portion of the at least one wafer.

25. The system of claim 24, wherein the processor is further configured to:
identify at least one region within the resolution-enhanced topography map having high frequency topography variations;
determine a location for positioning at least one dummy-fill within the at least one identified region based on the at least one identified region; and
produce a modified pattern layout corresponding to the at least one wafer to include the at least one dummy-fill within the at least one identified region.

26. The system of claim 24, wherein the processor is further configured to:
calibrate a design simulation model at least partially based on the resolution-enhanced topography map.

* * * * *